US012573506B2

(12) United States Patent
Nakanishi

(10) Patent No.: US 12,573,506 B2
(45) Date of Patent: Mar. 10, 2026

(54) PREDICTION SYSTEM, PREDICTION DEVICE, AND PREDICTION METHOD

(71) Applicant: KANEKA CORPORATION, Osaka (JP)

(72) Inventor: Hidekazu Nakanishi, Settsu (JP)

(73) Assignee: KANEKA CORPORATION, Osaka (JP)

( * ) Notice: Subject to any disclaimer, the term of this patent is extended or adjusted under 35 U.S.C. 154(b) by 53 days.

(21) Appl. No.: 18/640,432

(22) Filed: Apr. 19, 2024

(65) Prior Publication Data

US 2024/0266057 A1 Aug. 8, 2024

Related U.S. Application Data

(63) Continuation of application No. PCT/JP2022/037269, filed on Oct. 5, 2022.

(30) Foreign Application Priority Data

Oct. 21, 2021 (JP) .................................. 2021-172086
Oct. 21, 2021 (JP) .................................. 2021-172087

(51) Int. Cl.
*G16H 50/20* (2018.01)

(52) U.S. Cl.
CPC .................................. *G16H 50/20* (2018.01)

(58) Field of Classification Search
CPC ........ G16H 50/20; G16H 30/40; G16H 50/00; G16H 30/00; G16H 50/70; A61B 10/00
See application file for complete search history.

(56) References Cited

U.S. PATENT DOCUMENTS

2017/0046839 A1* 2/2017 Paik ........................ G06V 10/84
2017/0140109 A1* 5/2017 Kheifetz ................ G16H 50/50
2018/0078312 A1* 3/2018 Trayanova .............. G06T 19/00
(Continued)

FOREIGN PATENT DOCUMENTS

JP 2017-502439 A 1/2017
JP 2018-183567 A 11/2018
(Continued)

OTHER PUBLICATIONS

Kamal H, Lopez V, Sheth SA. Machine Learning in Acute Ischemic Stroke Neuroimaging. Front Neurol. Nov. 8, 2018;9:945. doi: 10.3389/fneur.2018.00945. PMID: 30467491; PMCID: PMC6236025. (Year: 2018).*

(Continued)

*Primary Examiner* — Sun M Li
(74) *Attorney, Agent, or Firm* — Osha Bergman Watanabe & Burton LLP

(57) ABSTRACT

A prediction system includes: a terminal; and a processor, communicatively coupled to the processor. The processor is configured to: acquire medical treatment information including images captured at at least one of before, during, immediately after, and after a predetermined period from treatment of a patient with a symptom of a vascular disease; classify a condition of the patient based on a classification image; learn the medical treatment information in association with the condition of the patient; and predict at least one of a treatment effect and a prognosis when treatment intervention is performed for the patient based on a learning result.

11 Claims, 2 Drawing Sheets

(56) References Cited

U.S. PATENT DOCUMENTS

| | | | |
|---|---|---|---|
| 2019/0246904 A1* | 8/2019 | Kim | A61B 5/7246 |
| 2020/0202527 A1* | 6/2020 | Choi | G06T 5/73 |
| 2020/0315518 A1* | 10/2020 | Chun | G16H 50/70 |
| 2021/0241909 A1* | 8/2021 | Bulut | G16H 20/00 |
| 2021/0251577 A1* | 8/2021 | Itu | G06N 3/0455 |
| 2021/0338330 A1* | 11/2021 | Rao | A61B 34/10 |
| 2022/0108801 A1* | 4/2022 | Yamazaki | G16H 15/00 |
| 2022/0246301 A1* | 8/2022 | Choi | G16H 50/70 |

FOREIGN PATENT DOCUMENTS

| | | | |
|---|---|---|---|
| JP | 2018-196742 A | 12/2018 | |
| JP | 2020-506012 A | 2/2020 | |
| JP | 2020-121049 A | 8/2020 | |
| JP | 2020-127672 A | 8/2020 | |
| JP | 2021-033919 A | 3/2021 | |
| WO | 2015/082555 A1 | 6/2015 | |
| WO | 2015/153362 A1 | 10/2015 | |
| WO | WO-2020231007 A2 * | 11/2020 | G06N 3/045 |

OTHER PUBLICATIONS

Chen Q, Wang Y, Qiu Y, Wu X, Zhou Y, Zhai G. A Deep Learning-Based Model for Classification of Different Subtypes of Subcortical Vascular Cognitive Impairment With FLAIR. Front Neurosci. Jun. 18, 2020;14:557. doi: 10.3389/fnins.2020.00557. PMID: 32625048; PMCID: PMC7315844. (Year: 2020).*

Mascitelli JR, Moyle H, Oermann EK, et al An update to the Raymond-Roy Occlusion Classification of intracranial aneurysms treated with coil embolization Journal of Neuro Interventional Surgery 2015;7:496-502. (Year: 2015).*

J. -S. Hong et al., "Machine Learning Application With Quantitative Digital Subtraction Angiography for Detection of Hemorrhagic Brain Arteriovenous Malformations," in IEEE Access, vol. 8, pp. 204573-204584, 2020, doi: 10.1109/Access.2020.3036692. (Year: 2020).*

Ur DJ, Sugeng L. Non-invasive Multimodality Cardiovascular Imaging of the Right Heart and Pulmonary Circulation in Pulmonary Hypertension. Front Cardiovasc Med. Mar. 14, 2019;6:24. doi: 10.3389/fcvm.2019.00024. PMID: 30931315; PMCID: PMC6427926. (Year: 2019).*

International Search Report issued in International Application No. PCT/JP2022/037269 mailed Nov. 29, 2022 (4 pages).

* cited by examiner

PREDICTION SYSTEM, PREDICTION DEVICE, AND PREDICTION METHOD

TECHNICAL FIELD

The present invention relates to a prediction system, a prediction device, and a prediction method.

Priority is claimed on Japanese Patent Application No. 2021-172086 and Japanese Patent Application No. 2021-172087, filed Oct. 21, 2021, the contents of which are incorporated herein by reference.

BACKGROUND

Techniques for predicting cases of a disease in the future based on lifestyle habits using machine learning or deep learning are known. In addition, techniques for diagnosing patients using machine learning or deep learning based on medical images are known.

For example, Patent Document 1 discloses extracting case information similar to a patient's symptoms and changes in symptoms after starting medication.

In addition, Patent Document 2 discloses that an index of a coil filling rate for an aneurysm is output based on a three-dimensional medical image of the aneurysm, an X-ray image of the aneurysm, and a learning model, and an image showing a coil filling state is generated based on the index.

Furthermore, Patent Document 3 discloses that the possibility of existence of a pathological condition of interest is learned based on a normal image in which there is no pathological condition of interest such as a thrombus or a hematoma and an abnormal image in which there is a pathological condition of interest such as a thrombus or a hematoma by machine learning, and color information is added to a region on an image in which a pathological condition of interest is highly likely to exist.

[Patent Document 1]

Japanese Unexamined Patent Application, First Publication No. 2021-33919

[Patent Document 2]

Japanese Unexamined Patent Application, First Publication No. 2020-127672

[Patent Document 3]

Japanese Unexamined Patent Application, First Publication No. 2020-121049

However, a treatment effect and prognosis through treatment intervention for vascular diseases need to be predicted based on the experience of physicians. For this reason, it has been difficult for inexperienced doctors to predict a treatment effect and prognosis through treatment intervention for vascular diseases even when there are similar cases. Further, in hemorrhagic vascular diseases, even when it is possible to assist an operator by outputting a coil filling rate and a coil filling state when coil embolization is performed on a disease site, it is difficult to predict treatment effects and prognosis through treatment intervention. Further, in ischemic vascular diseases, even when it is possible to assist in specifying a disease site by coloring a region in which a pathological condition of interest is highly likely to exist such as a thrombus or a hematoma, it is not possible to predict treatment effects and prognosis through treatment intervention.

In this manner, when the related art is used for vascular diseases, it has been difficult to predict a treatment effect and prognosis through treatment intervention. Furthermore, it has been difficult to predict treatment effects and prognosis through objective treatment intervention for vascular diseases.

SUMMARY

One or more embodiments of the invention provide a prediction system, a prediction device, a prediction method, and a program which are capable of predict a treatment effect and prognosis.

A prediction system according to one aspect of the present invention includes an acquisition unit that acquires medical treatment information including images captured at at least one of before, during, immediately after, and after treatment of a patient with a symptom of a hemorrhagic or ischemic vascular disease, a classification unit that classifies a condition of the patient who has been treated for a hemorrhagic or ischemic vascular disease based on the image captured immediately after or after the treatment, a learning unit that learns by associating the medical treatment information with the condition of the patient who has been treated for a hemorrhagic or ischemic vascular disease, which is classified by the classification unit, and a prediction unit that predicts at least one of a treatment effect and prognosis when treatment intervention is performed for the patient with a symptom of a hemorrhagic or ischemic vascular disease based on a learning result.

Further, a prediction device according to one aspect of the present invention includes an acquisition unit that acquires medical treatment information including images captured at at least one of before, during, immediately after, and after treatment of a patient with a symptom of a hemorrhagic or ischemic vascular disease, a classification unit that classifies a condition of the patient who has been treated for a hemorrhagic or ischemic vascular disease based on the image captured immediately after or after the treatment, a learning unit that learns the medical treatment information in association with the condition of the patient who has been treated for a hemorrhagic or ischemic vascular disease, which is classified by the classification unit, and a prediction unit that predicts at least one of a treatment effect and prognosis when treatment intervention is performed for the patient with a symptom of a hemorrhagic or ischemic vascular disease based on a learning result.

In addition, a prediction method according to one aspect of the present invention causes a computer of a prediction device to execute steps of acquiring medical treatment information including images captured at at least one of before, during, immediately after, and after treatment of a patient with a symptom of a hemorrhagic or ischemic vascular disease, classifying a condition of the patient who has been treated for a hemorrhagic or ischemic vascular disease based on the image captured immediately after or after the treatment, learning the medical treatment information in association with the condition of the patient who has been treated for a hemorrhagic or ischemic vascular disease, which is classified by the classification unit, and predicting at least one of a treatment effect and prognosis when treatment intervention is performed for the patient with a symptom of a hemorrhagic or ischemic vascular disease based on a learning result.

These comprehensive or specific aspects may be realized by a system, a device, a method, an integrated circuit, a computer program, or a recording medium, or may be realized by any combination of the system, the device, the method, the integrated circuit, the computer program, and the recording medium.

According to one aspect of the present invention, it is possible to predict a treatment effect and prognosis.

DETAILED DESCRIPTION

Hereinafter, embodiments of the present invention will be described in detail with reference to the drawings.
<Configuration of Prediction System>

A prediction system according to one or more embodiments will be described with reference to FIG. 1.

Figures 1, 2:
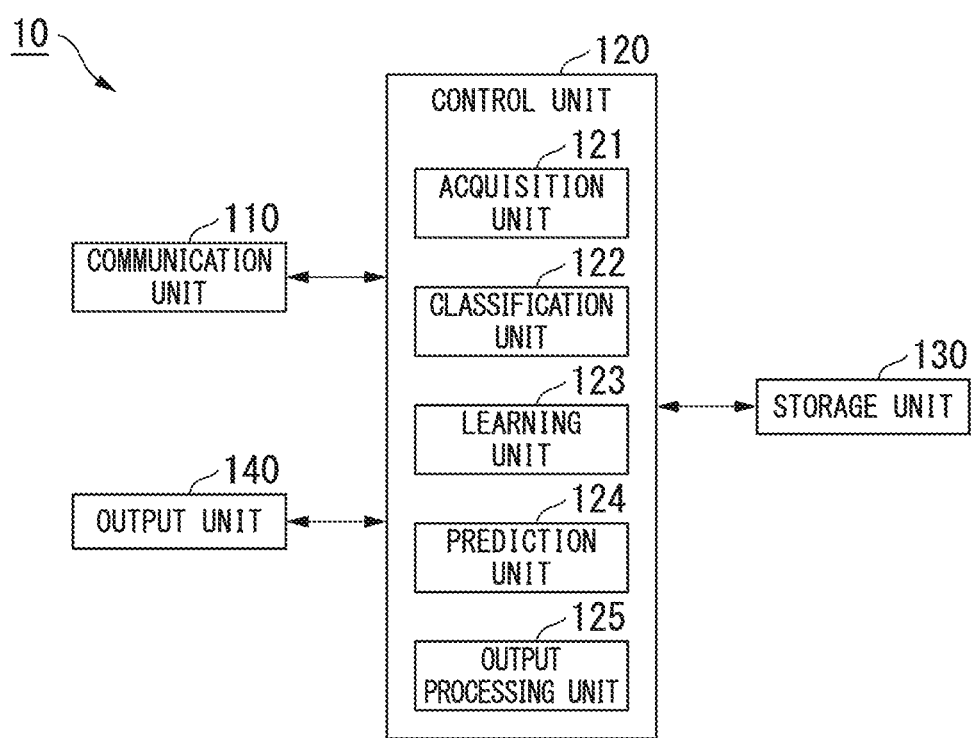
FIG. 1 is a schematic diagram of a prediction system according to one or more embodiments of the present invention.
FIG. 2 is a block diagram showing an example of a configuration of a prediction device according to one or more embodiments.

FIG. 1 is a schematic diagram of a prediction system 1 according to one or more embodiments. The prediction system 1 includes a prediction device 10 shown in FIG. 1 and a terminal device T. The prediction device 10 and the terminal device T are communicatively connected.

For each patient with a symptom of a vascular disease, the prediction device 10 stores learning results learned based on medical treatment information including images captured at at least one of before, during, immediately after, and after treatment, and the condition of a corresponding patient. Here, the "after treatment" means a timing after a predetermined period has passed immediately after treatment. The predetermined period is, for example, one week, one month, three months, six months, 12 months, one year, two years, five years, or the like. The medical treatment information is one or more of medical chart information and counseling information, including at least image information.

The medical chart information includes information such as identification information, the age, the gender, the nationality, medical examination information, a smoking history, and a medical history of a patient. The counseling information is information such as counseling audio when performing counseling for a patient, or sentences obtained from voice recognition for the audio.

The medical chart information may include medication information of a patient. The medication information of the patient is information on medicines taken for antiplatelet drugs, anticoagulants, or a combination thereof. The medication information of the patient may include adherence information. The adherence information is, for example, the type of medicine taken by the patient, a period over which a medicine is taken, and the status of taking medicines such as forgetting to take a medicine or self-discontinuation.

The image information includes medical images such as contrast images and captured images captured at at least one of before, during, immediately after, and after (e.g., after a predetermined period from) treatment. The contrast images are, for example, images captured using a contrast agent for a disease site. Further, the captured images are, for example, images captured by CT, MRI, PET, X-rays, tomosynthesis, echoes, an endoscope, a smartphone, or the like. The medical examination information includes a patient's symptoms, the progress of treatment, surgical records, and the like based on medical history interviews and medical examinations of a patient with a symptom of a vascular disease.

In addition, the condition of the patient includes survival or death of the patient (whether the patient is alive or not), changes in classification performed by a classification unit to be described below, whether the patient has a sequela, whether a disease has recurred or not, and the like.

The prediction device 10 is a device that predicts a treatment effect and/or prognosis of the patient with a symptom of a vascular disease based on medical treatment information and learning results. The prediction device 10 is, for example, a terminal device such as a personal computer (PC), a server device, a smartphone, or a tablet.

The terminal device T acquires medical treatment information of a patient P. The terminal device T is, for example, a PC, a server device, a smartphone, a tablet, or the like. For example, the terminal device T acquires the medical treatment information of the patient P generated by medical examination for the patient P which is performed by a doctor D. The terminal device T outputs a treatment effect for the patient P predicted by the prediction device 10 and/or prognosis as prediction results.

The prediction device 10 and the terminal device T may be configured integrally.

The prediction system 1 will be described in more detail.

The prediction system 1 according to one or more embodiments is a system that predicts a treatment effect of a vascular disease and predicts prognosis. Here, the vascular disease includes an ischemic event and a hemorrhagic event. The ischemic event is an ischemic disease such as a blood flow disorder due to a thrombus or the like, for example, a peripheral vascular disorder such as a cerebral infarction, a myocardial infarction, or arteriosclerosis obliterans. The hemorrhagic event is a disease that involves a risk of bleeding, such as an aneurysm such as an aortic aneurysm or a cerebral aneurysm, or an arterial dissection.

In one or more embodiments, as an example, description is given of a case where prediction of a treatment effect to be obtained when performing treatment intervention by machine learning and/or prediction of prognosis by machine learning is performed based on medical treatment information of a patient with a symptom of a vascular disease.
<Configuration of Prediction Device>

A configuration of the prediction device 10 according to one or more embodiments will be described with reference to FIG. 2. FIG. 2 is a block diagram showing an example of the configuration of the prediction device 10 according to one or more embodiments.

As shown in FIG. 2, the prediction device 10 includes a communication unit 110, a control unit 120, a storage unit 130, and an output unit 140.
<Communication Unit 110>

The communication unit 110 has a function of transmitting and receiving various information. The communication unit 110 may use either a wired communication method or a wireless communication method. For example, the communication unit 110 receives medical treatment information of a patient from a terminal device. Furthermore, the communication unit 110 outputs the received information to the control unit 120.
<Control Unit 120>

The control unit 120 has a function of controlling the overall operation of the prediction device 10. The function is realized, for example, by causing a Central Processing Unit (CPU) provided as hardware in the prediction device 10 to execute a program.

As shown in FIG. 2, the control unit 120 includes an acquisition unit 121, a classification unit 122, a learning unit 123, a prediction unit 124, and an output processing unit 125.

<Acquisition Unit 121>

The acquisition unit 121 has a function of acquiring various information. For example, the acquisition unit 121 acquires medical treatment information from the terminal device via the communication unit 110. The acquisition unit 121 causes the storage unit 130 to store the acquired medical treatment information.

<Classification Unit 122>

The classification unit 122 has a function of classifying various information. For example, the classification unit 122 classifies the condition of the patient based on medical treatment information. The classification unit 122 classifies the condition of the patient based on medical examination information included in the medical treatment information.

The medical examination information according to one or more embodiments includes, for example, an aneurysm size (length×width×depth), a diseased blood vessel site, aneurysm sizes (the diameter of the aneurysm, the thickness of an aneurysm wall, the diameter of an aneurysm cervix, and the like), the diameter of a parent vessel, a volume embolization rate, a neck-dome ratio of an aneurysm size, the shape of the aneurysm, Modified-Raymond-Roy classification immediately after treatment, a treatment method (surgical treatment, endovascular treatment, a coil type, a flow diverter (FD), an intercircular device (ISD), the presence or absence of a stent), Modified-Raymond-Roy classification after treatment, a patient's symptoms, and the like.

The classification unit 122 classifies the condition of the patient based on at least one or more of the treatment method, the aneurysm size (length×width×depth), the diseased blood vessel site, the aneurysm sizes (the diameter of the aneurysm, the thickness of an aneurysm wall, an aneurysm cervix diameter, and the like), the parent vessel diameter, the volume embolization rate, the neck-dome ratio of the aneurysm size, the shape of the aneurysm included in the medical examination information.

Further, the medical examination information according to one or more embodiments may include, for example, an embolus site, an embolus size, a National Institute of Health Stroke Score (NIHSS) score before treatment, whether a tissue-type plasminogen activator (t-PA) has been administered, a period of time from the appearance of a symptom to t-PA administration, time, a period of time from t-PA administration to puncture, a treatment method (mechanical retrieval, thrombus aspiration, combination), the number of aneurysm recanalizations, a NIHSS score immediately after treatment, a NIHSS score after treatment, whether rehabilitation has been made, the type of rehabilitation, the patient's symptoms, and the like.

In this case, the classification unit 122 classifies the condition of the patient based on at least one or more of a treatment method, a NIHSS score before treatment, a NIHSS score immediately after treatment, and a NIHSS score after treatment included in the medical examination information.

The classification unit 122 classifies the condition of the patient in accordance with an image (e.g., a classification image, an image captured immediately after the treatment, an image captured after a predetermined period from the treatment) included in the medical treatment information. When the image included in the medical treatment information acquired by the acquisition unit 121 is an image before or during treatment, the classification unit 122 may not classify the condition of the patient for the image.

Here, there are various treatments for each of the ischemic event and hemorrhagic event. Treatment for the ischemic event includes thrombolytic therapy (t-PA administration), endovascular therapy (a stent retriever, a suction catheter, a combination system of a stent retriever and a suction catheter, a thrombus removal system in which a stent retriever and a suction catheter are combined, or the like), antithrombotic therapy (an antiplatelet drug, an antithrombin drugs, an anticoagulant, or the like), and the like. Treatment for the hemorrhagic event includes clipping surgery, coil embolization, stent placement, FD placement, ISD placement, vascular occlusion combined with bypass, artificial blood vessel replacement, stent graft insertion, and the like.

The classification unit 122 classifies the condition of the patient using classification indexes corresponding to a treatment method. The classification unit 122 stores a classification result in the storage unit 130 in association with the medical treatment information. When the medical treatment information and the classification result of the same identification information are stored in the storage unit 130, the classification unit 122 stores a correspondence relationship between medical treatment information and a classification result to be newly stored in the storage unit 130 in association with the already stored correspondence relationship between the medical treatment information and the classification result.

Here, the classification index is an index for classifying to which of a plurality of classes the condition of the patient belongs. In one or more embodiments, the classification index be set in accordance with an event or a treatment method of a vascular disease. For example, the classification index is an index such as a National Institute of Health Stroke Score (NIHSS) score, a Modified Rankin scale, an Evans index, Stanford classification, DeBaky classification, Raymond classification, or Modified-Raymond-Roy classification.

For example, when coil embolization for a hemorrhagic event is used, the classification unit 122 classifies to which class of the Modified-Raymond-Roy classification the image included in the medical treatment information belongs. The Modified-Raymond-Roy classification is an index classified into four classes, that is, class 1: complete occlusion, class 2: non-complete occlusion of the cervix, class 3a: non-complete occlusion inside the aneurysm, and class 3b: non-complete occlusion on the side of the aneurysm. The class 1 is a state in which the aneurysm is completely occluded by embolic coils or matrix tissue. The class 2 is a state in which the cervix of the aneurysm, called the neck, is not occluded by embolic coils or matrix tissue. The class 3a is a state in which the density of the embolic coils or the matrix tissue inside the aneurysm is lower than that in the case of the complete occlusion in the class 1, and the aneurysm remains. The class 3b is a state in which a portion of the aneurysm is not occluded by embolic coils or matrix-ing tissue.

Furthermore, for example, in the case of the ischemic event, the classification unit 122 classifies to which class the image included in the medical treatment information belongs by using an Evans index. The Evans index is an index expressed by a ratio between a maximum width between anterior horns of lateral ventricles on both sides and an intracranial cavity width in its cross section. For example, the classification unit 122 classifies the condition of the patient by classifying to which class the image included in the medical treatment information belongs in accordance with whether the Evans index is equal to or greater than a predetermined value.

Further, for example, in the case of an ischemic event, the classification unit 122 classifies to which class the medical examination information included in the medical treatment information belongs by using a NIHSS score. The NIHSS score is an index for evaluating stroke neurological severity. For example, the classification unit 122 classifies the condition of the patient by classifying to which class the medical examination information included in the medical treatment information belongs, in accordance with to which score range the NIHSS score belongs.

For example, in the case of an ischemic event, the classification unit 122 may classify the condition of the patient by classifying to which of predetermined classification criteria the medical examination information included in the medical treatment information belongs, in accordance with a position where a blood flow disorder is caused by a thrombus or the like, a vascular site (type) in which a blood flow disorder is caused by a thrombus or the like, a range in which a blood flow disorder is caused by a thrombus or the like, and the proportion of white and red thrombi based on the image included in the medical treatment information. The classification criteria are criteria for performing classification into at least two or more classes based on a blood vessel diameter, a blood vessel type, a blood vessel site, the size of a blood flow disorder, and the like.

<Learning Unit 123>

The learning unit 123 has a function of generating a regression model. The regression model according to one or more embodiments is a model in which medical treatment information and a classification result are associated. The learning unit 123 causes the storage unit 130 to store the generated regression model.

The learning unit 123 generates, for example, a regression model indicating a relationship between medical treatment information and a classification result, based on the medical treatment information and the classification result. When the medical treatment information is input, the generated regression model outputs the classification result according to the medical treatment information.

The learning unit 123 generates a regression model by, for example, statistical analysis. Specifically, the learning unit 123 generates a regression model based on a classification result obtained by the classification unit 122 and medical treatment information. Specifically, the learning unit 123 generates a model for classifying the condition of the patient based on the medical treatment information.

For example, when medical treatment information is input, a learned regression model outputs a classification result based on the medical treatment information and the learning model.

The learning unit 123 may generate a regression model indicating a relationship between medical treatment information, medication information, and a classification result based on the medical treatment information, the medication information, and the classification result. In this case, when the medical treatment information is input, the generated regression model outputs the classification result according to the medication information. Specifically, the medical treatment information is input, a learned regression model outputs classification results for the presence or absence of information on medicines taken for and adherence information, for example, medication information such as a period over which a medicine is taken, a status of taking medicines, and the type of medicine.

In addition, the learning unit 123 may generate a regression model (learned model) by machine learning. Examples of a machine learning method include SVR (support vector regression), random forest, deep learning using a neural network, and the like.

The learning unit 123 generates a learned model by, for example, supervised learning. In the supervised learning, learning using a data set for training for a learning model is performed. The data set is a set of explanatory variables that are input during learning and objective variables indicating a correct answer of data which is output based on the input data. The learning unit 123 performs verification using a data set for verification for a learned model constructed through training. The learning unit 123 determines the accuracy of a learning model constructed through verification using a data set for a test.

In one or more embodiments, explanatory variables are medical treatment information. The objective variables are treatment results based on classification results obtained by the classification unit 122. The learning unit 123 generates a learned model that has learned correspondence between medical treatment information and a classification result.

In this manner, it is possible to improve the accuracy of prediction performed by the prediction unit 124, which will be described later.

In one or more embodiments, the data set for training and the data set for verification include 12 million or more images, and the data set for a test include 1 million or more images.

In one or more embodiments, accuracy determination of a learning model using a data set for a test is not performed a plurality of times. That is, the accuracy determination of the learning model using the data set for a test may be performed once. In this manner, it is possible to suppress learning of a data set for a test.

Further, the learning unit 123 may perform clustering for each case based on medical treatment information. For example, the learning unit 123 may perform clustering by calculating a feature amount for each case and determining similarity, dissimilarity, and specificity of the feature amount. Further, the learning unit 123 may perform reinforcement learning by combining classification machine learning and regression machine learning. Thereby, it is possible to improve prediction accuracy.

<Prediction Unit 124>

The prediction unit 124 has a function of predicting a treatment effect and/or prognosis based on a classification result. For example, the prediction unit 124 predicts the classification result based on medical treatment information and a regression model as a treatment effect and/or prognosis.

Specifically, the prediction unit 124 inputs medical treatment information of a patient with a symptom of a vascular disease to a regression model generated in advance by the learning unit 123 and stored in the storage unit 130. The regression model having the medical treatment information input thereto outputs classification results. Based on the classification results output by the regression model, the prediction unit 124 predicts treatment effects and/or prognosis such as changes in classification after a predetermined period of time (for example, one year), changes in symptom, a recovery rate, a recurrence rate (for example, a recanalization rate through coil compaction), a survival rate, whether rehabilitation has been made, and the type of rehabilitation. The treatment effect and/or prognosis may be quantified based on the classification results. Here, the coil compaction is a phenomenon in which coil are compressed due to a blood flow within the aneurysm or a change in the direction of the blood flow, a coil mass is reduced, and a gap is formed within the aneurysm.

In one or more embodiments, the regression model outputs classification results as predictions of a treatment effect and/or prognosis.

In this manner, the prediction unit 124 can easily predict a treatment effect and prognosis simply by inputting medical treatment information to the regression model.

<Output Processing Unit 125>

The output processing unit 125 has a function of controlling output information of prediction results of a treatment effect and/or prognosis. For example, the output processing unit 125 inputs the prediction results predicted by the prediction unit 124 to the output unit 140 as information on a treatment effect and/or prognosis and causes the output unit 140 to display the prediction results.

<Storage Unit 130>

The storage unit 130 has a function of storing various information. The storage unit 130 is a storage medium such as a hard disk drive (HDD), a solid state drive (SSD), a flash memory, an electrically erasable programmable read only memory (EEPROM), a random access read/write memory (RAM), a read only memory (ROM), or any combination of these storage media.

<Output Unit 140>

The output unit 140 has a function of outputting various information. The function of the output unit 140 is realized by a display device such as a display included in the prediction device 10. The output unit 140 displays information on a treatment effect and/or prognosis which is input from the output processing unit 125.

The output unit 140 may be a display device included in a device other than the prediction device 10.

<Flow of Processing>

A flow of processing in the prediction system 1 according to one or more embodiments will be described with reference to FIGS. 3 and 4.

<Regression Model Generation Processing>

Figure 3:
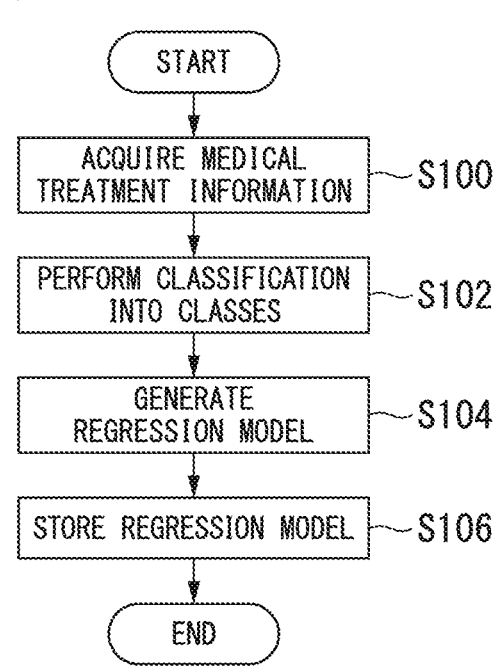
FIG. 3 is a flowchart showing a flow of regression model generation processing in the prediction system according to one or more embodiments.

FIG. 3 is a flowchart showing a flow of regression model generation processing in the prediction system 1 according to one or more embodiments.

As shown in FIG. 3, first, the acquisition unit 121 of the prediction device 10 acquires medical treatment information (step S100). Next, the classification unit 122 classifies to which class the medical treatment information acquired by the acquisition unit 121 belongs (step S102). Next, the learning unit 123 generates a regression model based on a classification result obtained by the classification unit 122 and the medical treatment information acquired by the acquisition unit 121 (step S104). Then, the learning unit 123 causes the storage unit 130 to store the generated regression model (step S106).

<Prediction Processing of Treatment Effect and/or Prognosis>

Figure 4:
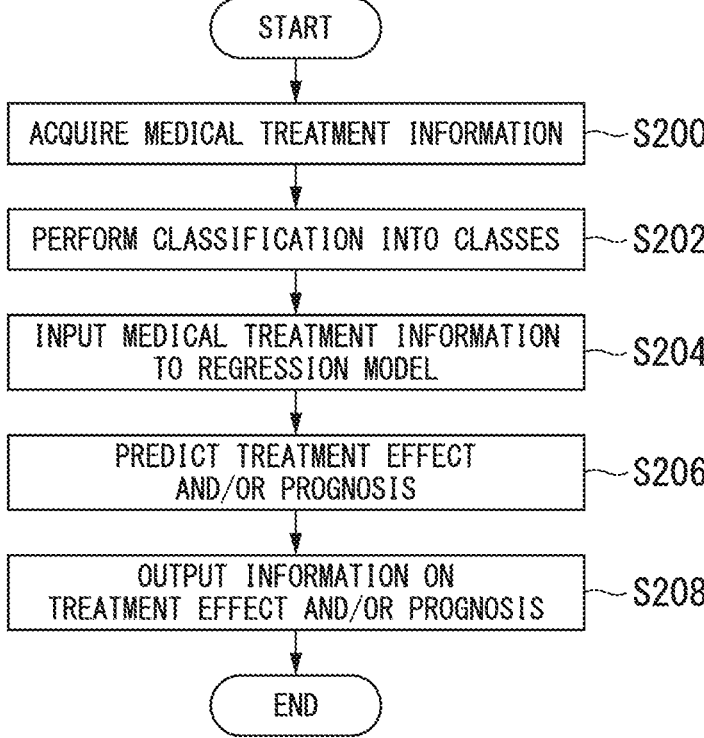
FIG. 4 is a flowchart showing a flow of prediction processing in the prediction system according one or more embodiments.

FIG. 4 is a flowchart showing a flow of prediction processing of a treatment effect and/or prognosis in the prediction system 1 according to one or more embodiments.

As shown in FIG. 4, first, the acquisition unit 121 of the prediction device 10 acquires medical treatment information (step S200). Next, the classification unit 122 classifies to which class the medical treatment information acquired by the acquisition unit 121 belongs (step S202). Next, the prediction unit 124 inputs the medical treatment information to the regression model stored in the storage unit 130 (step S204). The regression model outputs a classification result according to the input medical treatment information.

The prediction unit 124 predicts the classification result output by the regression model as information on a treatment effect and/or prognosis (step S206). The output processing unit 125 outputs the information on the treatment effect and/or prognosis predicted by the prediction unit 124 to the output unit 140 and causes the output unit 140 to display it (step S208).

As described above, the acquisition unit 121 of the prediction system 1 according to one or more embodiments acquires medical treatment information including images captured at at least one of before, during, immediately after, and after treatment of a patient with a symptom of a hemorrhagic vascular disease. The classification unit 122 classifies the condition of the patient who has been treated for a hemorrhagic vascular disease, based on the image captured immediately after or after the treatment. The learning unit 123 learns the medical treatment information and the condition of the patient with been treated for a hemorrhagic vascular disease, which is classified by the classification unit 122, in association with each other. The prediction unit 124 predicts at least one of a treatment effect and prognosis based on a learning result obtained by the learning unit 123 when treatment intervention is performed on the patient with a symptom of a hemorrhagic vascular disease.

Thereby, the prediction system 1 according to one or more embodiments can predict a treatment effect and/or prognosis by simply inputting medical treatment information before or during treatment to a regression model in which medical treatment information and a classification result are associated. Furthermore, an objective treatment effect and/or prognosis can be predicted by inputting medical treatment information including images to a regression model, and thus, it is possible to assist inexperienced doctors. In addition, by using medical treatment information including images, it is possible to perform integrated learning using not only image information but also a plurality of pieces of information such as medical chart information, medical examination information, and counseling information, which can improve prediction accuracy.

Modification Example

Embodiments of the present invention has been described above. Next, modification examples of the embodiments of the present invention will be described. The modification examples to be described below may be independently applied to the embodiments of the present invention or may be applied to the embodiments of the present invention in combination. Further, the modification examples may be applied instead of the configuration described in the embodiments of the present invention or may be applied in addition to the configuration described in the embodiments of the present invention.

In the above-described embodiments, an example of a case where treatment effects and/or prognosis of a hemorrhagic vascular disease and an ischemic vascular disease has been described, but prognosis regarding the state of a shunt used for hemodialysis may be predicted. In this case, a potassium concentration, a renal function evaluation value (GFR value), and the like may be used as classification indexes.

In the above-described embodiments, an example of a case where treatment effects and/or prognosis of a hemorrhagic vascular disease and an ischemic vascular disease has been described, but prognosis regarding the state of a peripheral arterial disease may be predicted. In this case, Fontaine classification or Rutherford classification may be used as classification indexes. In the case of a peripheral arterial disease, changes in the skin color of hands and feet may occur. In this case, for example, an image captured by a patient using a smartphone or the like may be used as a medical image. In addition, by learning and predicting the state of a peripheral arterial disease, such as the degree of progression, using medical treatment information such as medical chart information, counseling information, and medical examination information, together with the medical image, prognosis of the state of the peripheral arterial disease can be predicted.

In the above-described embodiments, description has been given of a case where an image is captured at at least one of before, during, immediately after, and after treatment which is a timing after a certain period of time has elapsed immediately after the treatment. However, an image may be captured at a timing before or during surgery, or an image may be obtained by simulation at a timing before or during surgery. In this case, in each step of the surgery, the effect of performing the next step can be predicted before performing the next step.

In addition, when the above-described surgery is any one of coil embolization, stent placement, flow diverter (FD) placement, or intercircular device (ISD) placement, changes in a blood flow due to the use of each surgical technique may be predicted. In this case, the changes in a blood flow may be dynamically predicted using images before and during surgery.

(Means 1) A prediction system including:

an acquisition unit that acquires medical treatment information including images captured at at least one of before, during, immediately after, and after treatment, and after treatment of a patient with a symptom of a hemorrhagic vascular disease;

a classification unit that classifies the condition of the patient who has been treated for a hemorrhagic vascular disease based on the image captured immediately after or after the treatment;

a learning unit that learns the medical treatment information in association with the condition of the patient who has been treated for a hemorrhagic vascular disease, which is classified by the classification unit; and a prediction unit that predicts at least one of a treatment effect and prognosis when treatment intervention is performed for the patient with a symptom of a hemorrhagic vascular disease based on a learning result.

(Means 2) The prediction system according to (Means 1), wherein the classification unit performs classification based on at least one of the image captured immediately after treatment and the image captured after a certain period of time has elapsed after treatment.

(Means 3) The prediction system according to (Means 1) or (Means 2), wherein the classification unit performs classification using Modified-Raymond-Roy classification.

(Means 4) The prediction system according to any one of (Means 1) to (Means 3), wherein the learning unit performs clustering on each piece of medical treatment information acquired by the acquisition unit.

(Means 5) The prediction system according to any one of (means 1) to (means 4), wherein the hemorrhagic vascular disease is an aneurysm, and the learning unit performs learning based on the diameter of the aneurysm, the thickness of an aneurysm wall, the diameter of an aneurysm cervix, the diameter of a parent vessel, and the shape of the aneurysm in the image.

(Means 6) The prediction system according to any one of (Means 1) to (Means 5), wherein the learning unit performs learning using a model obtained by learning and a model that does not use teaching data classified from actual treatment results.

(Means 7) The prediction system according to any one of (Means 1) to (Means 6), wherein the acquisition unit acquires medical treatment information including images captured before and during surgery, and the prediction unit predicts an effect of proceeding to the next step in surgery for the patient with a symptom of a hemorrhagic vascular disease.

(Means 8) A prediction device including:

an acquisition unit that acquires medical treatment information including images captured at at least one of before, during, immediately after, and after treatment, and after treatment of a patient with a symptom of a hemorrhagic vascular disease;

a classification unit that classifies a condition of the patient who has been treated for a hemorrhagic vascular disease based on the image captured immediately after or after the treatment;

a learning unit that learns the medical treatment information in association with the condition of the patient who has been treated for a hemorrhagic vascular disease, which is classified by the classification unit; and an output unit that outputs at least one of a predicted treatment effect and a predicted prognosis when treatment intervention is performed for the patient with a symptom of a hemorrhagic vascular disease based on a learning result.

(Means 9) A prediction method of causing a computer to execute processes of:

an acquisition process of acquiring medical treatment information including images captured at at least one of before, during, immediately after, and after treatment, and after treatment of a patient with a symptom of a hemorrhagic vascular disease;

a classification process of classifying a condition of the patient who has been treated for a hemorrhagic vascular disease based on the image captured immediately after or after the treatment;

a learning process of learning the medical treatment information in association with the condition of the patient who has been treated for a hemorrhagic vascular disease, which is classified in the classification process; and a prediction process of predicting at least one of a treatment effect and prognosis when treatment intervention is performed for the patient with a symptom of a hemorrhagic vascular disease based on a learning result.

(Means 10) A program causing a computer to execute steps of:

an acquisition step of acquiring medical treatment information including images captured at at least one of before, during, immediately after, and after treatment, and after treatment of a patient with a symptom of a hemorrhagic vascular disease;

a classification step of classifying a condition of the patient who has been treated for a hemorrhagic vascular disease based on the image captured immediately after or after the treatment;

a learning step of learning the medical treatment information in association with the condition of the patient who has been treated for a hemorrhagic vascular disease, which is classified in the classification step; and a prediction step of predicting at least one of a treatment effect and prognosis when treatment intervention is performed for the patient with a symptom of a hemor-rhagic vascular disease based on a learning result.

Hereinafter, additional embodiments of the present invention will be described in detail with reference to the drawings.

The following description will be made with reference to the drawings used in the above-described embodiments.

<Configuration of Prediction System>

A prediction system according to one or more embodiments will be described with reference to FIG. 1.

FIG. 1 is a schematic diagram of a prediction system 1 according to one or more embodiments. The prediction system 1 includes the prediction device 10 shown in FIG. 1 and a terminal device T. The prediction device 10 and the terminal device T are communicably connected.

For each patient with a symptom of a vascular disease, the prediction device 10 stores learning results learned based on medical treatment information including images captured at at least one of before, during, immediately after, and after treatment, and the condition of a corresponding patient. Here, the "after treatment" means a timing after a predetermined period has passed immediately after treatment. The predetermined period is, for example, one week, one month, three months, six months, 12 months, one year, two years, five years, or the like. The medical treatment information is one or more of medical chart information and counseling information, including at least image information.

The medical chart information includes information such as identification information, the age, the gender, the nationality, medical examination information, a smoking history, and a medical history of a patient. The counseling information is information such as a counseling voice when performing counseling for a patient, or sentences obtained by voice recognition of the voice.

The medical chart information may include medication information of a patient. The medication information of the patient is information on medicines taken for antiplatelet drugs, anticoagulants, diabetic drugs, hyperlipidemic drugs, diuretics, antihypertensives, vasopressors, or combinations thereof. The medication information of the patient may include adherence information. The adherence information is information such as the type of medicine taken by the patient, a period over which a medicine is taken, and a status of taking medicines such as forgetting to take a medicine or self-discontinuation.

The image information is information on medical images such as contrast images and captured images captured at at least one of before, during, immediately after, and after treatment. The contrast images are, for example, images captured using a contrast agent for a disease site. Further, the captured images are, for example, images captured by CT, MRI, PET, X-rays, tomosynthesis, echoes, an endoscope, a smartphone, or the like. The medical examination information includes a patient's symptom, the progress of treatment, surgical records, and the like based on history taking and medical examination of a patient with a symptom of a vascular disease.

In addition, the condition of the patient includes lift or death of the patient (whether the patient is alive or not), changes in classification performed by a classification unit to be described below, whether the patient has a sequela, whether a disease has recurred or not, and the like.

The prediction device 10 is a device that predicts a treatment effect and/or prognosis of the patient with a symptom of a vascular disease based on medical treatment information and learning results. The prediction device 10 is, for example, a terminal device such as a personal computer (PC), a server device, a smartphone, or a tablet.

The terminal device T acquires medical treatment information of a patient P. The terminal device T is, for example, a PC, a server device, a smartphone, a tablet, or the like. For example, the terminal device T acquires the medical treatment information of the patient P generated by medical examination for the patient P which is performed by a doctor D. The terminal device T outputs a treatment effect for the patient P predicted by the prediction device 10 and/or prognosis as prediction results.

The prediction device 10 and the terminal device T may be configured integrally.

The prediction system 1 will be described in more detail. The prediction system 1 according to one or more embodiments is a system that predicts a treatment effect of a vascular disease and predicts prognosis. Here, the vascular disease includes an ischemic event and a hemorrhagic event. The ischemic event is an ischemic disease such as a blood flow disorder due to a thrombus or the like, for example, a peripheral vascular disorder such as a cerebral infarction, a myocardial infarction, or arteriosclerosis obliterans. The hemorrhagic event is a disease that involves a risk of bleeding, such as an aneurysm such as an aortic aneurysm or a cerebral aneurysm, or an arterial dissection.

In one or more embodiments, as an example, description is given of a case where prediction of a treatment effect to be obtained when performing treatment intervention by machine learning and/or prediction of prognosis by machine learning is performed based on medical treatment information of a patient with a symptom of a vascular disease.

<Configuration of Prediction Device>

A configuration of the prediction device 10 according to one or more embodiments will be described with reference to FIG. 2. FIG. 2 is a block diagram showing an example of the configuration of the prediction device 10 according to one or more embodiments.

As shown in FIG. 2, the prediction device 10 includes a communication unit 110, a control unit 120, a storage unit 130, and an output unit 140.

<Communication Unit 110>

The communication unit 110 has a function of transmitting and receiving various information. The communication unit 110 may use either a wired communication method or a wireless communication method. For example, the communication unit 110 receives medical treatment information of a patient from a terminal device. Furthermore, the communication unit 110 outputs the received information to the control unit 120.

<Control Unit 120>

The control unit 120 (e.g., a processor, a processor communicatively coupled to a terminal, a processor of a terminal) has a function of controlling the overall operation of the prediction device 10. The function is realized, for example, by causing a Central Processing Unit (CPU) provided as hardware in the prediction device 10 to execute a program.

As shown in FIG. 2, the control unit 120 includes an acquisition unit 121, a classification unit 122, a learning unit 123, a prediction unit 124, and an output processing unit 125.

<Acquisition Unit 121>

The acquisition unit 121 has a function of acquiring various information. For example, the acquisition unit 121 acquires medical treatment information. The acquisition unit 121 causes the storage unit 130 to store the acquired medical treatment information.

<Classification Unit 122>

The classification unit 122 has a function of classifying various information. For example, the classification unit 122 classifies the condition of the patient based on medical treatment information. The classification unit 122 classifies the condition of the patient based on medical examination information included in the medical treatment information.

The medical examination information according to one or more embodiments includes, for example, an aneurysm size (length×width×depth), a diseased blood vessel site, aneurysm sizes (the diameter of the aneurysm, the thickness of an aneurysm wall, the diameter of an aneurysm cervix, and the like), the diameter of a parent vessel, a volume embolization rate, a neck-dome ratio of an aneurysm size, the shape of the aneurysm, Modified-Raymond-Roy classification immediately after treatment, a treatment method (surgical treatment, endovascular treatment, a coil type, FD, ISD, the presence or absence of a stent), Modified-Raymond-Roy classification after treatment, a patient's symptoms, and the like.

The classification unit 122 classifies the condition of the patient based on at least one or more of the treatment method, the aneurysm size (length×width×depth), the diseased blood vessel site, the aneurysm sizes (the diameter of the aneurysm, the thickness of an aneurysm wall, an aneurysm cervix diameter, and the like), the parent vessel diameter, the volume embolization rate, the neck-dome ratio of the aneurysm size, the shape of the aneurysm included in the medical examination information.

Further, the medical examination information according to one or more embodiments may include, for example, an embolus site, an embolus size, a National Institute of Health Stroke Score (NIHSS) score before treatment, whether a tissue-type plasminogen activator (t-PA) has been administered, a period of time from the appearance of a symptom to t-PA administration, time, a period of time from t-PA administration to puncture, a treatment method (mechanical retrieval, thrombus aspiration, combination), the number of aneurysm recanalizations, a NIHSS score immediately after treatment, a NIHSS score after treatment, whether rehabilitation has been made, the type of rehabilitation, the patient's symptoms, and the like.

In this case, the classification unit 122 classifies the condition of the patient based on at least one or more of a treatment method, a NIHSS score before treatment, a NIHSS score immediately after treatment, and a NIHSS score after treatment included in the medical examination information.

The classification unit 122 classifies the condition of the patient in accordance with an image included in the medical treatment information. When the image included in the medical treatment information acquired by the acquisition unit 121 is an image before or during treatment, the classification unit 122 may not classify the condition of the patient for the image.

Here, there are various treatments for each of the ischemic event and hemorrhagic event. Treatment for the ischemic event includes thrombolytic therapy (t-PA administration), endovascular therapy (a stent retriever, a suction catheter, a combination system of a stent retriever and a suction catheter, a thrombus removal system in which a stent retriever and a suction catheter are combined, or the like), antithrombotic therapy (an antiplatelet drug, an antithrombin drugs, an anticoagulant, or the like), and the like. Treatment for the hemorrhagic event includes clipping surgery, coil embolization, stent placement, FD placement, vascular occlusion combined with bypass, artificial blood vessel replacement, stent graft insertion, and the like.

The classification unit 122 classifies the condition of the patient according to the image included in the medical treatment information by using classification indexes corresponding to a treatment method. The classification unit 122 stores a classification result in the storage unit 130 in association with the medical treatment information. When the medical treatment information and the classification result of the same identification information are stored in the storage unit 130, the classification unit 122 stores a correspondence relationship between medical treatment information and a classification result to be newly stored in the storage unit 130 in association with the already stored correspondence relationship between the medical treatment information and the classification result.

Here, the classification index is an index for classifying to which of a plurality of classes the condition of the patient belongs. In one or more embodiments, the classification index is set in accordance with an event or a treatment method of a vascular disease. For example, the classification index is an index such as a National Institute of Health Stroke Score (NIHSS) score, a Modified Rankin scale, an Evans index, Stanford classification, DeBaky classification, Raymond classification, or Modified-Raymond-Roy classification.

For example, when coil embolization for a hemorrhagic event is used, the classification unit 122 classifies to which class of the Modified-Raymond-Roy classification the image included in the medical treatment information belongs. The Modified-Raymond-Roy classification is an index classified into four classes, that is, class 1: complete occlusion, class 2: non-complete occlusion of the cervix, class 3a: non-complete occlusion inside the aneurysm, and class 3b: non-complete occlusion on the side of the aneurysm. The class 1 is a state in which the aneurysm is completely occluded by embolic coils or matrix tissue. The class 2 is a state in which the cervix of the aneurysm, called the neck, is not occluded by embolic coils or matrix tissue. The class 3a is a state in which the density of the embolic coils or the matrix tissue inside the aneurysm is lower than that in the case of the complete occlusion in the class 1, and the aneurysm remains. The class 3b is a state in which a portion of the aneurysm is not occluded by embolic coils or matrixing tissue.

Furthermore, for example, in the case of the ischemic event, the classification unit 122 classifies to which class the image included in the medical treatment information belongs by using an Evans index. The Evans index is an index expressed by the ratio between the maximum width between anterior horns of lateral ventricles on both sides and an intracranial cavity width in its cross section. For example, the classification unit 122 classifies the condition of the patient by classifying to which class the image included in the medical treatment information belongs in accordance with whether the Evans index is equal to or greater than a predetermined value.

Further, for example, in the case of an ischemic event, the classification unit 122 classifies to which class the medical examination information included in the medical treatment information belongs by using a NIHSS score. The NIHSS score is an index for evaluating stroke neurological severity. For example, the classification unit 122 classifies the condition of the patient by classifying to which class the medical examination information included in the medical treatment information belongs, in accordance with to which score range the NIHSS score belongs.

For example, in the case of an ischemic event, the classification unit 122 may classify the condition of the patient by classifying to which of predetermined classification criteria the medical examination information included in the medical treatment information belongs, in accordance with a position where a blood flow disorder is caused by a thrombus or the like, a vascular site (type) in which a blood flow disorder is caused by a thrombus or the like, and a range in which a blood flow disorder is caused by a thrombus or the like based on the image included in the medical treatment information. The classification criteria are criteria for performing classification into at least two or more classes based on a blood vessel diameter, a blood vessel type, a blood vessel site, the size of a blood flow disorder, and the like.

<Learning Unit 123>

The learning unit 123 has a function of generating a regression model. The regression model according to one or more embodiments is a model in which medical treatment information and a classification result are associated. The learning unit 123 causes the storage unit 130 to store the generated regression model.

The learning unit 123 generates, for example, a regression model indicating a relationship between medical treatment information and a classification result, based on the medical treatment information and the classification result. When the medical treatment information is input, the generated regression model outputs the classification result according to the medical treatment information.

The learning unit 123 generates a regression model by, for example, statistical analysis. Specifically, the learning unit 123 generates a regression model based on a classification result obtained by the classification unit 122 and medical treatment information. Specifically, the learning unit 123 generates a model for classifying the condition of the patient based on the medical treatment information.

For example, when medical treatment information is input, a learned regression model outputs a classification result based on the medical treatment information and the learning model.

The learning unit 123 may generate a regression model indicating a relationship between medical treatment information, medication information, and a classification result based on the medical treatment information, the medication information, and the classification result. In this case, when the medical treatment information is input, the generated regression model outputs the classification result according to the medication information. Specifically, the medical treatment information is input, a learned regression model outputs classification results for the presence or absence of information on medicines taken for and adherence information, for example, medication information such as a period over which a medicine is taken, a status of taking medicines, and the type of medicine.

In addition, the learning unit 123 may generate a regression model (learned model) by machine learning. Examples of a machine learning method include SVR (support vector regression), random forest, deep learning using a neural network, and the like.

The learning unit 123 generates a learned model by, for example, supervised learning. In the supervised learning, learning using a data set for training for a learning model is performed. The data set is a set of explanatory variables that are input during learning and objective variables indicating a correct answer of data which is output based on the input data. The learning unit 123 performs verification using a data set for verification for a learned model constructed through training. The learning unit 123 determines the accuracy of a learning model constructed through verification using a data set for a test.

In one or more embodiments, explanatory variables are medical treatment information. The objective variables are treatment results based on classification results obtained by the classification unit 122. The learning unit 123 generates a learned model that has learned correspondence between medical treatment information and a classification result.

In this manner, it is possible to improve the accuracy of prediction performed by the prediction unit 124, which will be described later.

In one or more embodiments, the data set for training and the data set for verification include 12 million or more images, and the data set for a test include 1 million or more images.

In one or more embodiments, accuracy determination of a learning model using a data set for a test is not performed a plurality of times and, in some embodiments, may be performed once. In this manner, it is possible to suppress learning of a data set for a test.

Further, the learning unit 123 may perform clustering for each case based on medical treatment information. For example, the learning unit 123 may perform clustering by calculating a feature amount for each case and determining similarity, dissimilarity, and specificity of the feature amount. Further, the learning unit 123 may perform reinforcement learning by combining classification machine learning and regression machine learning. Thereby, it is possible to improve prediction accuracy.

<Prediction Unit 124>

The prediction unit 124 has a function of predicting a treatment effect and/or prognosis based on a classification result. For example, the prediction unit 124 predicts the classification result based on medical treatment information and a regression model as a treatment effect and/or prognosis.

Specifically, the prediction unit 124 inputs medical treatment information of a patient with a symptom of a vascular disease to a regression model generated in advance by the learning unit 123 and stored in the storage unit 130. The regression model having the medical treatment information input thereto outputs classification results. Based on the classification results output by the regression model, the prediction unit 124 predicts treatment effects and/or prognosis such as changes in classification after a predetermined period of time (for example, one year), changes in symptom, a recovery rate, a recurrence rate, a survival rate, whether rehabilitation has been made, and the type of rehabilitation. The treatment effect and/or prognosis may be quantified based on the classification results.

In one or more embodiments, the regression model outputs classification results as predictions of a treatment effect and/or prognosis.

In this manner, the prediction unit 124 can easily predict a treatment effect and prognosis simply by inputting medical treatment information to the regression model.

<Output Processing Unit 125>

The output processing unit 125 has a function of controlling output information of prediction results of a treatment effect and/or prognosis. For example, the output processing unit 125 inputs the prediction results predicted by the prediction unit 124 to the output unit 140 as information on a treatment effect and/or prognosis and causes the output unit 140 to display the prediction results.

<Storage Unit 130>

The storage unit 130 has a function of storing various information. The storage unit 130 is a storage medium such as a hard disk drive (HDD), a solid state drive (SSD), a flash memory, an electrically erasable programmable read only memory (EEPROM), a random access read/write memory (RAM), a read only memory (ROM), or any combination of these storage media.

<Output Unit 140>

The output unit 140 has a function of outputting various information. The function of the output unit 140 is realized by a display device such as a display included in the prediction device 10. The output unit 140 displays information on a treatment effect and/or prognosis which is input from the output processing unit 125.

The output unit 140 may be a display device included in a device other than the prediction device 10.

<Flow of Processing>

A flow of processing in the prediction system 1 according to one or more embodiments will be described with reference to FIGS. 3 and 4.

<Regression Model Generation Processing>

FIG. 3 is a flowchart showing a flow of regression model generation processing in the prediction system 1 according to one or more embodiments.

As shown in FIG. 3, first, the acquisition unit 121 of the prediction device 10 acquires medical treatment information (step S100). Next, the classification unit 122 classifies to which class the medical treatment information acquired by the acquisition unit 121 belongs (step S102). Next, the learning unit 123 generates a regression model based on a classification result obtained by the classification unit 122 and the medical treatment information acquired by the acquisition unit 121 (step S104). Then, the learning unit 123 causes the storage unit 130 to store the generated regression model (step S106).

<Prediction Processing of Treatment Effect and/or Prognosis>

FIG. 4 is a flowchart showing a flow of prediction processing of a treatment effect and/or prognosis in the prediction system 1 according to one or more embodiments.

As shown in FIG. 4, first, the acquisition unit 121 of the prediction device 10 acquires medical treatment information (step S200). Next, the classification unit 122 classifies to which class the medical treatment information acquired by the acquisition unit 121 belongs (step S202). Next, the prediction unit 124 inputs the medical treatment information to the regression model stored in the storage unit 130 (step S204). The regression model outputs a classification result according to the input medical treatment information.

The prediction unit 124 predicts the classification result output by the regression model as information on a treatment effect and/or prognosis (step S206). The output processing unit 125 outputs the information on the treatment effect and/or prognosis predicted by the prediction unit 124 to the output unit 140 and causes the output unit 140 to display it (step S208).

As described above, the acquisition unit 121 of the prediction system 1 according to one or more embodiments acquires medical treatment information including one or both of images, which are captured at at least one of before, during, immediately after, and after treatment of a patient with a symptom of an ischemic vascular disease, and a severity evaluation table. The classification unit 122 classifies the condition of the patient who has treated for an ischemic vascular disease, based on the image captured immediately after or after the treatment or the severity evaluation table. The learning unit 123 learns the medical treatment information and the condition of the patient with been treated for an ischemic vascular disease, which is classified by the classification unit 122, in association with each other. The prediction unit 124 predicts at least one of a treatment effect and prognosis based on a learning result obtained by the learning unit 123 when treatment intervention is performed on the patient with a symptom of an ischemic vascular disease.

Thereby, the prediction system 1 according to one or more embodiments can predict a treatment effect and/or prognosis by simply inputting medical treatment information before or during treatment to a regression model in which medical treatment information and a classification result are associated. Furthermore, an objective treatment effect and/or prognosis can be predicted by inputting medical treatment information including images to a regression model, and thus it is possible to assist inexperienced doctors. In addition, by using medical treatment information including images, it is possible to perform integrated learning using not only image information but also a plurality of pieces of information such as medical chart information, medical examination information, and counseling information, which can improve prediction accuracy.

Modification Example

Embodiments of the present invention has been described above. Next, modification examples of the embodiments of the present invention will be described. The modification examples to be described below may be independently applied to the embodiments of the present invention or may be applied to the embodiments of the present invention in combination. Further, the modification examples may be applied instead of the configuration described in the embodiments of the present invention, or may be applied in addition to the configuration described in the embodiments of the present invention.

In the above-described embodiments, an example of a case where treatment effects and/or prognosis of a hemorrhagic vascular disease and an ischemic vascular disease has been described, but prognosis regarding the state of a shunt used for hemodialysis may be predicted. In this case, a potassium concentration, a renal function evaluation value (GFR value) and the like may be used as classification indexes.

In the above-described embodiments, an example of a case where treatment effects and/or prognosis of a hemorrhagic vascular disease and an ischemic vascular disease has been described, but prognosis regarding the state of a peripheral arterial disease may be predicted. In this case, Fontaine classification or Rutherford classification may be used as classification indexes. In the case of a peripheral arterial disease, changes in the skin color of hands and feet may occur. In this case, for example, an image captured by a patient using a smartphone or the like may be used as a medical image. In addition, by learning and predicting the state of a peripheral arterial disease, such as the degree of progression, using medical treatment information such as medical chart information, counseling information, and medical examination information, together with the medical image, prognosis of the state of the peripheral arterial disease can be predicted.

In the above-described embodiments, description has been given of a case where an image is captured at at least one of before, during, immediately after, and after treatment which is a timing after a certain period of time has elapsed immediately after the treatment. However, an image may be captured at a timing before or during surgery, or an image may be obtained by simulation at a timing before or during surgery. In this case, in each step of the surgery, the effect of performing the next step can be predicted before performing the next step.

In addition, when the above-described surgery is any one of coil embolization, stent placement, or flow diverter placement, changes in a blood flow due to the use of each surgical technique may be predicted. In this case, the changes in a blood flow may be dynamically predicted using images before and during surgery.

(Means 11) A prediction system including:

an acquisition unit that acquires medical treatment information including one or both of images, which are captured at at least one of before, during, immediately after, and after treatment of a patient with a symptom of an ischemic vascular disease, and a severity evaluation table;

a classification unit that classifies the condition of the patient who has treated for an ischemic vascular disease, based on the image captured immediately after or after the treatment or the severity evaluation table;

a learning unit that learns the medical treatment information and the condition of the patient with been treated for an ischemic vascular disease, which is classified by the classification unit, in association with each other; and a prediction unit that predicts at least one of a treatment effect and prognosis based on a learning result when treatment intervention is performed on the patient with a symptom of an ischemic vascular disease.

(Means 12) The prediction system according to (means 11), wherein the classification unit performs classification using any one of a National Institute of Health Stroke Score, a Modified Rankin scale, an Evans index, a Fontaine index, and a Rutherford index as the severity evaluation table.

(Means 13) The prediction system according to (Means 11) or (Means 12), wherein the learning unit performs clustering on each piece of medical treatment information acquired by the acquisition unit.

(Means 14) The prediction system according to any one of (Means 11) to (Means 13), wherein the learning unit performs learning using a model obtained by learning and a model that does not use teaching data classified from actual treatment results.

(Measure 15) A prediction device including:

an acquisition unit that acquires medical treatment information including one or both of images, which are captured at at least one of before, during, immediately after, and after treatment of a patient with a symptom of an ischemic vascular disease, and a severity evaluation table;

a classification unit that classifies the condition of the patient who has treated for an ischemic vascular disease, based on the image captured immediately after or after the treatment or the severity evaluation table;

a learning unit that learns the medical treatment information and the condition of the patient with been treated for an ischemic vascular disease, which is classified by the classification unit, in association with each other; and a prediction unit that predicts at least one of a treatment effect and prognosis based on a learning result when treatment intervention is performed on the patient with a symptom of an ischemic vascular disease.

(Means 16) A prediction method of causing a computer to execute processes of:

an acquisition process of acquiring medical treatment information including one or both of images, which are captured at at least one of before, during, immediately after, and after treatment of a patient with a symptom of an ischemic vascular disease, and a severity evaluation table;

a classification process of classifying the condition of the patient who has treated for an ischemic vascular disease, based on the image captured immediately after or after the treatment or the severity evaluation table;

a learning process of learning the medical treatment information and the condition of the patient with been treated for an ischemic vascular disease, which is classified in the classification process, in association with each other; and a prediction process of predicting at least one of a treatment effect and prognosis based on a learning result when treatment intervention is performed on the patient with a symptom of an ischemic vascular disease.

(Means 17) A program causing a computer to execute steps of:

an acquisition step of acquiring medical treatment information including one or both of images, which are captured at at least one of before, during, immediately after, and after treatment of a patient with a symptom of an ischemic vascular disease, and a severity evaluation table;

a classification step of classifying the condition of the patient who has treated for an ischemic vascular disease, based on the image captured immediately after or after the treatment or the severity evaluation table;

a learning step of learning the medical treatment information and the condition of the patient with been treated for an ischemic vascular disease, which is classified in the classification step, in association with each other; and a prediction step of predicting at least one of a treatment effect and prognosis based on a learning result when treatment intervention is performed on the patient with a symptom of an ischemic vascular disease.

A program running on a device according to an aspect of the present invention may be a program that controls a central processing unit (CPU) and the like to cause a computer to operate in such a manner as to realize the functions of the above-described embodiments according to the aspect of the present invention. Programs or information handled by the programs are temporarily read into a volatile memory, such as a random access memory (RAM) while being processed, or stored in a non-volatile memory, such as a flash memory, or a hard disk drive (HDD), and then read by the CPU to be modified or rewritten, as necessary.

The devices in the above-described embodiments may be partially implemented by a computer. In such a case, a program for realizing such control functions may be recorded on a computer-readable recording medium to cause a computer system to read the program recorded on the recording medium to execute the program. It is assumed that the "computer system" mentioned here refers to a computer system built into the devices, and the computer system includes an operating system and hardware such as a peripheral device. The "computer-readable recording medium" may be any of a semiconductor recording medium, an optical recording medium, a magnetic recording medium, and the like.

Furthermore, the "computer-readable recording medium" may include a medium that dynamically stores a program for a short period of time, such as a communication line that is used to transmit the program through a network such as the Internet or through a communication line such as a telephone line, and may also include a medium that stores a program for a fixed period of time, such as a volatile memory within the computer system for functioning as a server or a client in such a case. The above-described program may be configured to realize some of the functions described above, and additionally may be configured to realize the functions described above, in combination with a program already recorded in the computer system.

Each functional block or various characteristics of the devices used in the above-described embodiments may be implemented or performed on an electric circuit, that is, typically an integrated circuit or a plurality of integrated circuits. An electric circuit designed to execute the functions described in the present specification may include a general-purpose processor, a digital signal processor (DSP), an application specific integrated circuit (ASIC), a field programmable gate array (FPGA), or other programmable logic devices, discrete gates or transistor logics, discrete hardware components, or combinations thereof. The general-purpose processor may be a microprocessor, or the processor may be a processor of a known type, a controller, a micro-controller, or a state machine instead. The general-purpose processor or the above-mentioned circuits may be constituted by a digital circuit, or may be constituted by an analog circuit. When a circuit integration technology that replaces the present integrated circuits with advances in semiconductor technology appears, it is also possible to use an integrated circuit based on the technology.

Although the embodiments of the present invention have been described in detail above with reference to the drawings, the specific configuration is not limited to the embodiments and includes, for example, an amendment to a design that falls within the scope that does not depart from the gist of the present invention. Various modifications can be made within the scope of an aspect of the present invention defined by claims, and embodiments that are made by suitably combining technical means disclosed according to different embodiments are also included in the technical scope of the present invention. A configuration in which constituent elements, described in the embodiments and having mutually the same effects, are substituted for one another is also included in the technical scope of the present invention.

One aspect of the present invention can be used in, for example, a prediction system, a prediction device, an integrated circuit, a program, or the like.

REFERENCE SIGNS LIST

1 Prediction system
T Terminal device
10 Prediction device
110 Communication unit
120 Control unit
121 Acquisition unit
122 Classification unit
123 Learning unit
124 Prediction unit
125 Output processing unit
130 Storage unit
140 Output unit
What is claimed is:
1. A prediction system comprising:
a terminal;
a display device; and
a processor, communicatively coupled to the terminal and the display device, configured to:

acquire medical treatment information for a patient with a symptom of a vascular disease, the medical treatment information including:
  a treatment method that includes a surgery for the patient; and
  images captured at least one of before and during the surgery;
generate a classification result by inputting the medical treatment information into a machine learning model,
  wherein the machine learning model is a regression model trained by the processor to classify images of an aneurysm based on a diameter of the aneurysm, a diameter of an aneurysm cervix, a diameter of a parent vessel, a coil type, a flow diverter and a shape of the aneurysm and to output a Modified-Raymond-Roy classification as the classification result;
determine, based on the classification result, a prediction of at least one of a treatment effect and a prognosis of performing a step of the surgery before the step is performed for the patient,
  wherein the prediction includes a change in a blood flow associated with the classification result, and
  wherein the prediction is quantified based on the classification result; and
display the prediction on the display device.
2. The prediction system according to claim 1, wherein the processor is configured to perform clustering on each piece of the medical treatment information.
3. The prediction system according to claim 2, wherein the processor is configured to learn using a model obtained by learning and a model that does not use teaching data classified from actual treatment results.
4. The prediction system according to claim 2, wherein the processor is configured to learn by associating the medical treatment information, a condition of the patient, and medication information of the patient with each other.
5. The prediction system according to claim 1, wherein the vascular disease is an ischemic vascular disease,
the processor is configured to acquire a severity evaluation table included in the medical treatment information,
the regression model is trained to classify the images based on the severity evaluation table, and
the severity evaluation table is any one of:
  a National Institute of Health Stroke Score,
  a Modified Rankin scale,
  an Evans index,
  a Fontaine index, and
  a Rutherford index.
6. The prediction system according to claim 1, wherein the processor is configured to perform clustering on each piece of the medical treatment information.
7. The prediction system according to claim 6, wherein the processor is configured to learn using a model obtained by learning and a model that does not use teaching data classified from actual treatment results.
8. The prediction system according to claim 6, wherein the processor is configured to learn by associating the medical treatment information, a condition of the patient, and medication information of the patient with each other.
9. The prediction system according to claim 1, wherein the change in the blood flow is an inflow of a contrast agent into the aneurysm.

10. A prediction device including:

a processor, communicatively coupled to a display device, configured to:

acquire medical treatment information for a patient with a symptom of a vascular disease, the medical treatment information including:

a treatment method that includes a surgery for the patient; and images captured at least one of before and during the surgery;

generate a classification result by inputting the medical treatment information into a machine learning model, wherein the machine learning model is a regression model trained by the processor to classify images of an aneurysm based on a diameter of the aneurysm, a diameter of an aneurysm cervix, a diameter of a parent vessel, a coil type, a flow diverter and a shape of the aneurysm and to output a Modified-Raymond-Roy classification as the classification result;

determine, based on the classification result, a prediction of at least one of a treatment effect and a prognosis of performing a step of the surgery before the step is performed, wherein the prediction includes a change in a blood flow associated with the classification result, and wherein the prediction is quantified based on the classification result; and display the prediction on a display device.

11. A prediction method comprising:

acquiring medical treatment information for a patient with a symptom of a vascular disease, the medical treatment information including:

a treatment method that includes a surgery for the patient; and images captured at least one of before and during the surgery;

generating a classification result by inputting the medical treatment information into a machine learning model, wherein the machine learning model is a regression model trained to classify images of an aneurysm based on a diameter of the aneurysm, a diameter of an aneurysm cervix, a diameter of a parent vessel, a coil type, a flow diverter and a shape of the aneurysm and to output a Modified-Raymond-Roy classification as the classification result;

determining, based on the classification result, a prediction of at least one of a treatment effect and a prognosis of performing a step of the surgery before the step is performed for the patient, wherein the prediction includes a change in a blood flow associated with the classification result, and wherein the prediction is quantified based on the classification result; and display the prediction on the display device.

* * * * *